United States Patent [19]
Duncan et al.

[11] Patent Number: 5,690,631
[45] Date of Patent: Nov. 25, 1997

[54] MULTI-CONFIGURABLE PLATING SYSTEM

[75] Inventors: Jeffrey Duncan; Kevin Stone, both of Jacksonville, Fla.

[73] Assignee: Walter Lorenz Surgical, Inc., Jacksonville, Fla.

[21] Appl. No.: 712,431

[22] Filed: Sep. 11, 1996

[51] Int. Cl.⁶ .................................................. A61B 17/58
[52] U.S. Cl. .............................. 606/69; 606/70; 606/71; 606/72
[58] Field of Search ............................... 606/69, 70, 72, 606/60

[56] References Cited

U.S. PATENT DOCUMENTS

| | | |
|---|---|---|
| 1,105,105 | 7/1914 | Sherman . |
| 2,494,229 | 1/1950 | Collison . |
| 2,791,868 | 5/1957 | Viken . |
| 3,547,114 | 12/1970 | Haboush . |
| 3,779,240 | 12/1973 | Kondo . |
| 4,219,015 | 8/1980 | Steinmann . |
| 4,503,848 | 3/1985 | Casper et al. . |
| 4,683,878 | 8/1987 | Carter . |
| 4,793,335 | 12/1988 | Frey et al. . |
| 4,903,691 | 2/1990 | Heinl .......................... 606/70 |
| 4,905,679 | 3/1990 | Morgan . |
| 4,905,680 | 3/1990 | Tunc . |
| 5,087,202 | 2/1992 | Krenkel . |
| 5,201,737 | 4/1993 | Leibinger et al. . |
| 5,372,598 | 12/1994 | Luhr et al. . |
| 5,468,242 | 11/1995 | Reisberg ........................ 606/151 |

FOREIGN PATENT DOCUMENTS

| | | |
|---|---|---|
| 290138 | 11/1988 | European Pat. Off. . |
| 291632 | 11/1988 | European Pat. Off. . |
| 433852 | 6/1991 | European Pat. Off. . |
| 2386301 | 11/1978 | France ........................... 606/69 |
| 2631539 | 5/1988 | France . |
| 2806609 | 7/1979 | Germany . |

OTHER PUBLICATIONS

Hans G. Luhr, M.D., D.M.D., *Indications for Use of a Microsystem for Internal Fixation in Craniofacial Surgery*, J. of Craniofacial Surgery, vol. 1, No. 1, Jan., 1990, pp. 35–52.
Translation of G 85 23 003.8 (Germany), Bone Plate, Feb. 1986, Oswald Leibinger GmbH (Owner).
Codman & Shurtleff, *Neurosurgical Quality Instruments*, copyright 1965, pp. 10–13.
Howmedica International, Inc., *Vitallium—Verschiedene Implantate*, p. 54.
M.E. Müller, M. Allgöwer and H. Willenegger, *Manual of Internal Fixation*, copyright 1970, pp. 46 and 47.
U. Heim and K.M. Pfeiffer, *Internal Fixation of Small Fractures*, copyright 1974, 1982 and 1988, p. 60.
Walter Lorenz Surgical, Inc., *Surgical Instrument Catalog 5th Edition*, copyright© 1993, pp. 10–11.
Walter Lorenz Surgical, Inc., *1.5/2.0mm Combination Titanium Osteosynthesis System*, copyright 1994.
Leibinger LP, *Leibinger*, copyright 1995, (1 sheet).
*For The Few Who Know The Difference, TiMesh Inc.* (1 sheet).

*Primary Examiner*—Michael Buiz
*Assistant Examiner*—Daphna Shai
*Attorney, Agent, or Firm*—Harness, Dickey & Pierce, P.L.C.

[57] ABSTRACT

The invention relates to a multi-configurable plating system for use in osteosynthesis and a method therefore. The multi-configurable plating system includes a multi-configurable plate formed from a plurality of annular mounting tabs linked together by a plurality of linking members. The plurality of annular mounting tabs and the plurality of linking members form a separable straight plate, a separable L-shaped plate and a separable T-shaped plate. The separable straight plate is connected to the multi-configurable plate by no more than two linking members. The separable L-shaped plate is connected to the multi-configurable plate by no more than two linking members. The separable T-shaped plate is connected to the multi-configurable plate by no more than three linking members. This enables a user to easily separate the separable straight plate, the separable L-shaped plate and the separable T-shaped plate from the multi-configurable plate by cutting along the appropriate linking members.

27 Claims, 9 Drawing Sheets

| CONVENTIONAL PROFILE | CUTS FROM MULTI CONFIGURABLE PLATE OF FIG 5 | CUTS FROM GRID PANEL | CUTS FROM MESH PANEL |
|---|---|---|---|
| 2x2 L-plate | 2 | 5 | 7 |
| 3x2 L-plate | 2 | 6 | 8 |
| 3x3 T-plate | 3 | 10 | 12 |
| 2x2 angled L | 3 | NA | NA |
| 3x2 angled L | 3 | NA | NA |
| 3x3 angled T | 4 | NA | NA |
| double T | 6 | 13 | 14 |
| Z-plate | 4 | NA | NA |
| 2 hole straight | 2 | 3 | 5 |
| 4 hole straight | 2 | 5 | 6 |
| 8 hole straight | 5 | 9 | 10 |
| 16 hole straight | 9 | 17 | 18 |

5,690,631

MULTI-CONFIGURABLE PLATING SYSTEM

BACKGROUND OF THE INVENTION

1. Field of the Invention

This invention relates generally to osteosynthesis and, more particularly, to a multi-configurable plating system for cranial and facial osteosynthesis.

2. Discussion of the Related Art

During cranial and facial surgery it is sometimes necessary to surgically align, stabilize, fasten or join bone using mechanical means, known in the art as osteosynthesis. Use of cranial and facial osteosynthesis may arise during reconstructive, plastic or neuro surgery. For example, during reconstructive surgery, various portions of a fractured skull may be required to be surgically fastened or joined together using mechanical means. During neuro surgery, bone flaps which are removed to gain access to the brain generally require mechanical means to secure the bone flaps in place after the bone flaps are separated from the skull. During plastic surgery, various cranial and facial features may be modified by relocation of bone to provide a desired effect which also requires mechanical means to join or fasten the surgically separated bone.

The conventional mechanical means used to fasten, join, and secure in place the cranial and facial bones include preconfigured plates (see FIGS. 1A–1H), uniform grid panels (see FIG. 2), and flexible mesh (see FIG. 3). Each of these devices are generally secured or affixed to the scull by use of screws or other appropriate fastening mechanisms which joins and secures two portions of the bone in a substantially fixed relationship with respect to one another (see FIG. 4).

The preconfigured plates, as shown in FIGS. 1A–1H, are configured into numerous shapes and sizes and are selected by the surgeon during the surgical procedure depending on the surgeon's requirements. Some of the preconfigured shapes commonly utilized include L-shaped plates 10, Y-shaped plates 12, T-shaped plates 14, Z-shaped plates 16, square-shaped plates 18, triangular-shaped plates 20, straight plates 22 and arcuate-shaped plates 24. Each of these plates include annular tabs 26 linked together by linking members 28.

The uniform grid panel 30, as shown in FIG. 2, also includes the annular tabs 26 which are linked together with the linking members 28 somewhat similar to the preconfigured plates. In this manner, when the surgeon requires a particular shape, the surgeon can cut along the linking members 28 to form a desired configuration or shape.

Likewise, the flexible mesh 32, as shown in FIG. 3, is merely an interconnected series of members 34 forming the flexible mesh 32 similar to a screen. Here again, the surgeon cuts the mesh 32 into the desired configuration similar to the way a patch would be cut to cover a desired area.

As shown in FIG. 4, various preconfigured plates are shown affixed to a skull 36 with screws 38. For example an L-shaped plate 10, a Y-shaped plate 12, a T-shaped plate 14, a Z-shaped plate 16, a square-shaped plate 18, a triangular-shaped plate 20, a straight plate 22, and an arcuate-shaped plate 24 are each shown affixed to various portions of the skull 36 to fixedly hold and secure one portion of the bone relative to another portion of the bone. In addition, patches formed by the flexible mesh 32, as well as a portion of the uniform grid panel 30 are also shown affixed at various portions of the skull 36 with screws 38.

However, use of the above-identified bone fixation devices exhibit many disadvantages. For example, use of the preconfigured plates 10–24 requires stocking and maintaining a proper inventory of all the various shapes and sizes which may be required during surgery. Moreover, because the surgeon may not know what shape or size will be needed during surgery, all of the most common shapes used will need to be at hand and sterilized prior to use. This takes added time which increases the overall cost of the surgery.

Use of the grid panels 30 eliminates the need to stock many common shapes which have linking members 28 positioned about 90° relative to other linking members 28. However, the grid panels 30 also exhibit many disadvantages. Specifically, many conventional shapes cannot be formed from the grid panels 30. These shapes include preconfigured plates having angled or arcuate linking members 28 which are not perpendicular to other linking members 28, such as the Z-shaped plate 16 or the arcuate-shaped plate 24. Because of this, various preconfigured plates must also be stocked and maintained. In addition, the uniform grid panels 30 have a general checkerboard configuration where each internal annual tab 26 generally includes at least four linking members 28a, 28b, 28c and 28d. Therefore, many more cuts are required to be made across many linking members 28 in order to form simple conventional shapes. This increases the amount of time it takes to form the conventional shapes. Still further, the grid panels 30 are generally thinner than preconfigured plates. Therefore, even if the grid panels 30 are cut to resemble the shapes of the preconfigured plates, these cut panels do not exhibit the same structural and physical properties as the preconfigured plates.

Use of the flexible mesh 32 exhibits disadvantages similar to those of the grid panels 30. For instance, the flexible mesh 32 which is similar to a screen is much thinner than the preconfigured plates and therefore does not provide the same structural and physical properties as the preconfigured plates. Furthermore, extensive cutting is required in order shape the flexible mesh 32 into various required shapes and sizes. Still further, the flexible mesh 32 also does not have dedicated annular tabs 26 to receive mounting screws 38 which are connected by the linking members 28, but is merely formed with members 34 similar to a screen so that conventional shapes of the preconfigured plates can never be reproduced from the flexible mesh 32.

What is needed then is a multi-configurable plating system for a cranial and facial osteosynthesis which does not suffer from the above-mentioned disadvantages. This will, in turn, eliminate the need to stock numerous types of preconfigured plates having various shapes and sizes, provide a plating system having substantially the same structural integrity as preconfigured plates, reduce the amount of cutting required to generate conventional shapes, enable non-conventional shapes to be formed, and reduce the overall surgical time, as well as the overall surgical cost involved with cranial and facial osteosynthesis. It is, therefore, an object of the present invention to provide such a multi-configurable plating system and method therefore.

SUMMARY OF THE INVENTION

In accordance with the teachings of the present invention, a multi-configurable plating system for use in osteosynthesis is disclosed. The multi-configurable plating system is adapted to form separate multiple shaped plates from a single multi-configurable plate. This is basically achieved by separating the multiple shaped plates by cutting along the appropriate linking members.

In one preferred embodiment, a multi-configurable plate for use in osteosynthesis includes a plurality of annular tabs connected together by a plurality of linking members. The plurality of annular tabs and the plurality of linking members forms a separable straight plate, a separable T-shaped plate and a separable L-shaped plate. The separable straight plate is connected to the multi-configurable plate by no more than two linking members. The separable L-shaped plate is connected to the multi-configurable plate by no more than two linking members. The separable T-shaped plate is connected to the multi-configurable plate by no more than three linking members. This enables a user to easily separate the separable straight plate, the separable L-shaped plate and the separable T-shaped plate from the multi-configurable plate by cutting along the appropriate linking members.

In another preferred embodiment, a method for aligning and stabilizing a portion of a bone relative to another portion of the bone is disclosed. This method includes the initial step of forming a multi-configurable plate from a plurality of mounting tabs linked together by a plurality of linking members. A straight plate is formed from the plurality of mounting tabs and the plurality of linking members and is separated from the multi-configurable plate by cutting along no more than two linking members. A T-shaped plate is formed from the plurality of mounting tabs and the plurality of linking members and is separated from the multi-configurable plate by cutting along no more than two linking members. A T-shaped plate is formed from the plurality of mounting tabs and the plurality of linking members and is separated from the multi-configurable plate by cutting along no more than three linking members.

Use of the present invention provides a multi-configurable plating system for use in osteosynthesis. As a result, the aforementioned disadvantages associated with the currently available techniques for use in osteosynthesis have been substantially reduced or eliminated.

BRIEF DESCRIPTION OF THE DRAWINGS

Still other advantages of the present invention will become apparent to those skilled in the art after reading the following specification and by reference to the drawings in which.

DETAILED DESCRIPTION OF THE PREFERRED EMBODIMENT(S)

The following description of the preferred embodiments concerning a multi-configurable plating system for cranial and facial osteosynthesis is merely exemplary in nature and is in no way intended to limit the invention or its application or uses. Moreover, while the present invention is described in detail below with reference to cranial and facial osteosynthesis, it will be appreciated by those skilled in the art that the present invention is clearly not limited to cranial and facial osteosynthesis and may be utilized in various other surgical procedures.

Figure 5:
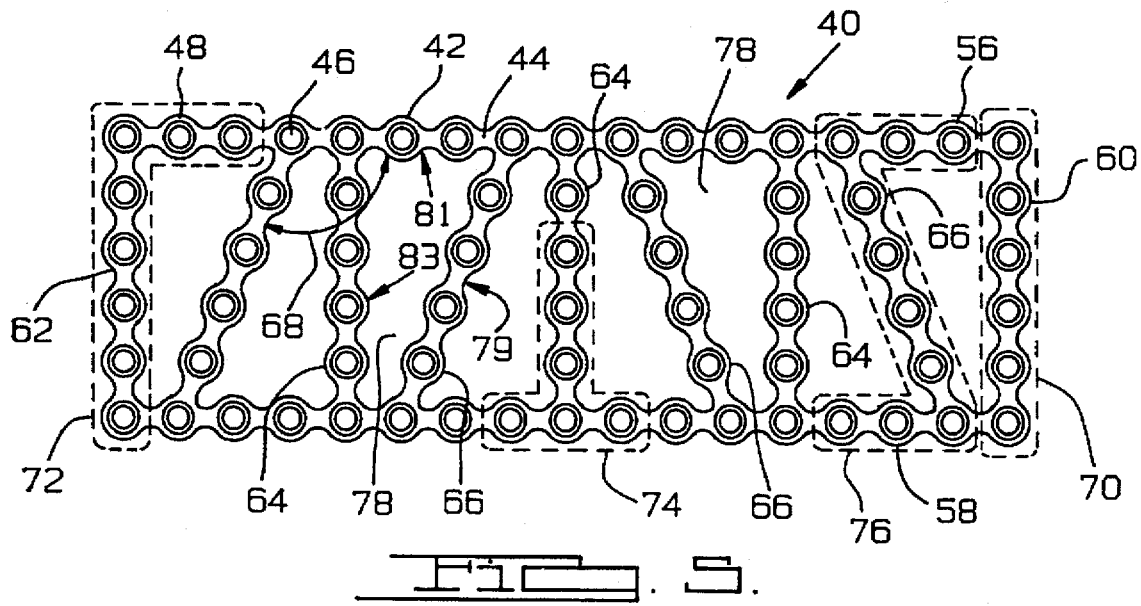
FIG. 5 is a top planar view of a multi-configurable plate according to the teachings of a first preferred embodiment of the present invention.

Referring to FIG. 5, a multi-configurable plate 40 according to the first preferred embodiment of the present invention is shown. The multi-configurable plate 40 is preferably constructed of titanium. However, the multi-configurable plate 40 may also be constructed of a titanium alloy, cobalt chrome, stainless steel, resorbable polymer or any other biocompatible implant material having preferably a malleable property so that the multi-configurable plate 40 may be shaped to conform to the curvature of the skull 36.

Figure 6:
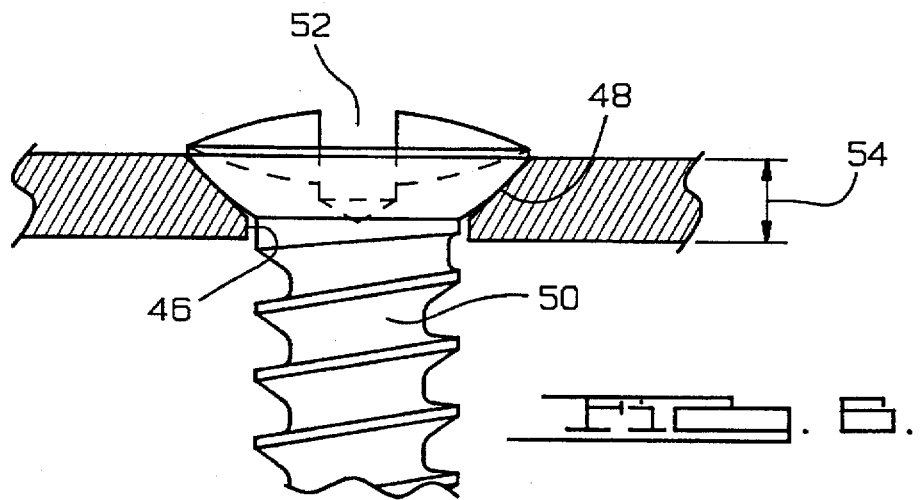
FIG. 6 is a partial side cross-sectional view of the multi-configurable plate of FIG. 5 illustrating one method of mounting the multi-configurable plate.

The multi-configurable plate 40 includes a plurality of annular mounting tabs 42 connected or linked together by a plurality of linking members 44. The annular mounting tabs 42 preferably have an inner diameter 46 in the range of between about 0.5 millimeters to about 3.5 millimeters, with 1.5 millimeter being the preferred diameter. Each annular mounting tab 42 includes a counterbore 48 which is operable to removably receive a mounting screw 50 or other suitable mounting device (see FIG. 6). The mounting screw 50 is also preferably constructed of titanium or other suitable material. The screw 50 includes a cross-drive head 52 or other suitable head such as a square-drive head or an internal hexagon-drive head.

The multi-configurable plate 40 has a substantially uniform thickness 54 in the range of between about 0.3 millimeters to about 1.5 millimeters. Preferably, the thickness 54 may either be 0.6 millimeters or 1.0 millimeter which are the same thicknesses generally offered in conventional preconfigured plates. This enables the multi-configurable plate 40 to exhibit substantially the same structural and physical properties of conventional preconfigured plates when formed to resemble these preconfigured plates. The thickness utilized will vary depending on whether the particular multi-configurable plate 40 will be used in a load bearing or a non-load bearing situation.

The multi-configurable plate 40 has an outer rectangular periphery which is bounded by a first 17-hole straight plate 56 being substantially parallel with a second 17-hole straight plate 58 and a third 6-hole straight plate 60 being substantially parallel with a fourth 6-hole straight plate 62. The first and second straight plates 56 and 58 are also substantially perpendicular to the third and fourth straight plates 60 and 62. Positioned substantially perpendicular to the straight plates 56 and 58 are a plurality of internal straight plates 64 which are connected to the straight plates 56 and 58 by only two linking members 44. Another plurality of internal straight plates 66 are also positioned oblique to the straight plates 56 and 58, each having an angle 68 of about 113.5° which represents an angle similar to the 110° angles used in some conventional preconfigured plates, such as Z-shaped plates.

From the multi-configurable plate 40, multiple separable plates can be formed by merely cutting along the appropriate linking members 44. For example, during normal use of the multi-configurable plate 40, a surgeon can generally form up to 12 separate non-integral plates out of the single multi-configurable plate 40. These non-integral plates include various shaped plates such as a 6-hole straight plate 70 which can be separated by merely cutting along two linking members 44. A 3×5 L-shaped plate 72 can be formed by also cutting along only two linking members 44. A T-shaped plate 74 can be formed by cutting along only three linking members 44. A Z-shaped plate 76 may be formed by cutting along only four linking members 44. In addition, it can be readily observed that various other standard preconfigured shapes, as well as non-standard shapes can be formed from the multi-configurable plate 40 by merely cutting along the appropriate linking members 44. It should also be noted that when a cut is made along a linking member 44, the linking member 44 may be trimmed such that only the outer circumference of the annular mounting tab 42 is exposed at the sides, thereby removing any squared edges.

Figure 7:
FIG. 7 is a chart which compares the first preferred embodiment with the prior art.

Referring to FIG. 7, a chart is shown which identifies the number of cuts required to form various conventional preconfigured plates from the multi-configurable plate 40 versus a standard grid panel 30 and a somewhat similar shape formed from a mesh panel 32. Upon review of this chart, one can see that several preconfigured shapes can be formed with a minimal number of cuts along linking members 44 verses the number of cuts required along linking members 28 in the grid panel 30 or along members 34 in the mesh panel 32. Moreover, several shaped plates cannot be formed from either the grid panel 30 or the mesh panel 32, most notably any panels containing angled or arcuate shaped members (see FIG. 13). In addition, the mesh panel 32 cannot form the same shapes of the preconfigured plates.

It should also be noted that the reason that several different shaped plates can be formed with a minimal number of cuts versus the conventional grid panel 30 is because of multiple separate internal peripheries or voids 78 situated within the outer periphery of the multi-configurable plate 40. The multiple internal peripheries or voids 78 are defined by the plurality of mounting tabs 42 linked together by the plurality of linking members 44. Each internal periphery 78 is bounded by at least three sides 79, 81 and 83, with each side formed by the plurality of mounting tabs 42 and the plurality of linking tabs 44. For example, side 79 is a straight side that is formed by six (6) mounting tabs 42 and five (5) linking members 44. Side 81 is a straight side formed by form (4) mounting tabs 42 and three (3) linking members 44. Side 83 is a straight side formed by six (6) mounting tabs and five (5) linking members 44. This eliminates the need to cut out unwanted and unneeded excess annular mounting tabs 42 which must be done with the uniform grid panel 30.

Figure 8:
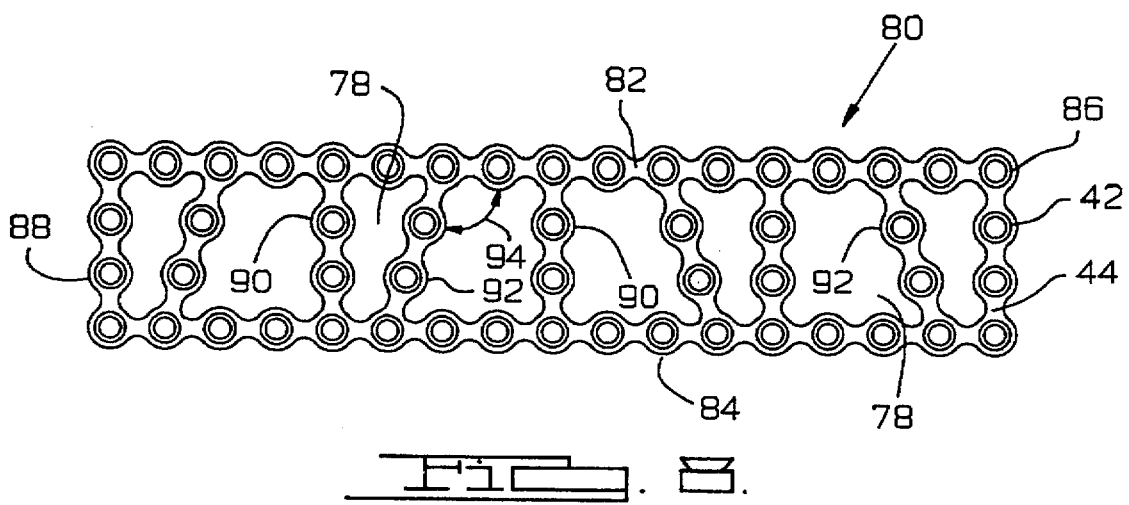
FIG. 8 is a top planar view of a multi-configurable plate according to the teachings of a second preferred embodiment of the present invention.

The second preferred embodiment of the present invention will now be described with reference to FIG. 8. In this regard, like reference numerals will be used to identify similar structures as described with respect to the other preferred embodiments of the present invention. A multi-configurable plate 80 according to the second preferred embodiment of the present invention includes the plurality of annular mounting tabs 42 linked together by the plurality of linking members 44 forming multiple internal peripheries or voids 78.

The multi-configurable plate 80 has an overall shape which somewhat mirrors the multi-configurable plate 40, shown in FIG. 5, except that the multi-configurable plate 80 is somewhat smaller than the multi-configurable plate 40. Specifically, the multi-configurable plate 80 includes two 17-hole straight plates 82 and 84 which are substantially parallel to one another and two 4-hole straight plates 86 and 88 which are substantially parallel to one another and perpendicular to the straight plates 82 and 84. The straight plates 82, 84, 86 and 88, form an outer rectangular periphery having a plurality of straight plates 90 connected substantially perpendicular to the straight plates 82 and 84 by only two linking members 44. A plurality of straight plates 92 are also positioned oblique to the straight plates 82 and 84 each having an angle 94 of about 109.5° which represents an angle similar to 110° angles used in some conventional preconfigured plates, such as Z-shaped plates. Here again, multiple separable plates can be formed by merely cutting along the appropriate linking members 44.

Figure 9:
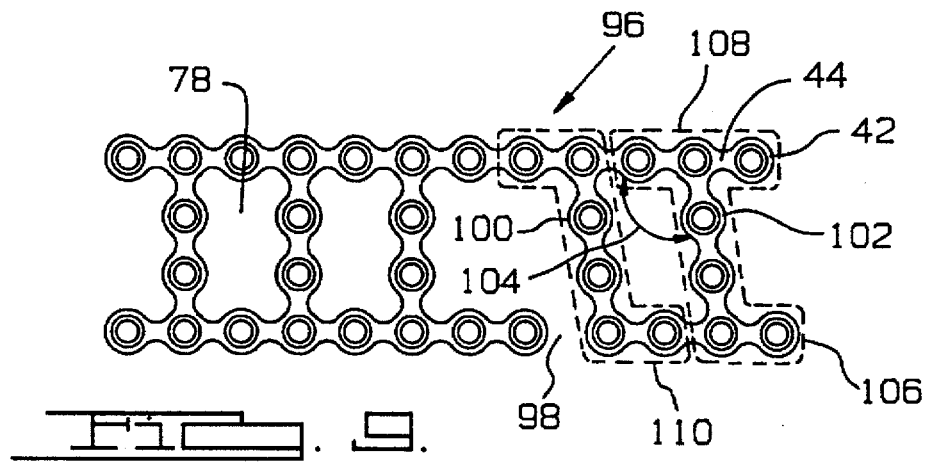
FIG. 9 is a top planar view of a multi-configurable plate according to the teachings of a third preferred embodiment of the present invention.

A third preferred embodiment of the present invention will now be described with reference to FIG. 9. A multi-configurable plate 96 according to the third preferred embodiment of the present invention also includes the plurality of annual mounting tabs 42 linked together by the plurality of linking members 44 forming multiple internal peripheries or voids 78. The multi-configurable plate 96 includes and defines a gap 98 which enables a pair of straight plates 100 and 102 which are substantially parallel to one another to form an angle 104° of 110° which is the exact angle used in some conventional preconfigured shapes. This enables the multi-configurable plate 96 to form an angled L-shaped plate 106, an angled T-shaped plate 108 and a Z-shaped plates 110 which are substantially identical to conventional angled preconfigured shaped plates, as well as other shaped plates.

Figure 10:
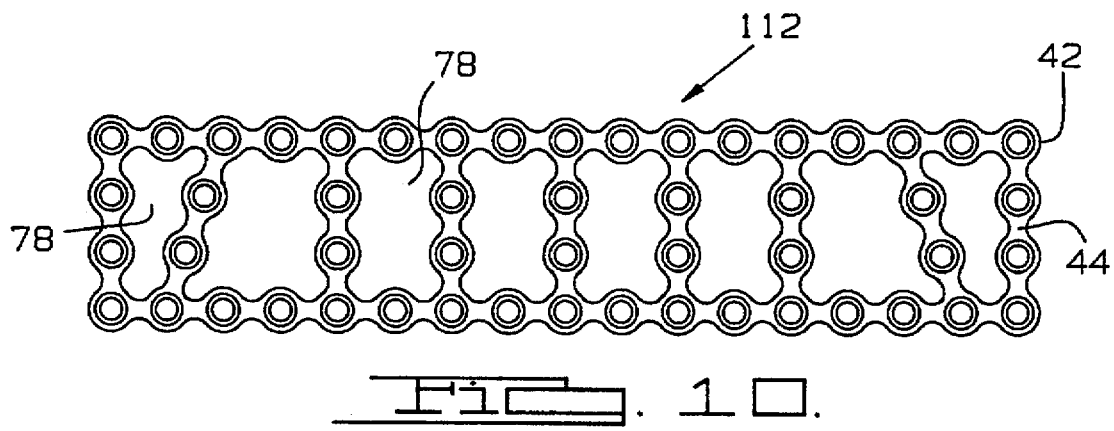
FIG. 10 is a top planar view of a multi-configurable plate according to the teachings of a fourth preferred embodiment of the present invention.

A fourth preferred embodiment of the present invention will now be described with reference to FIG. 10. A multi-configurable plate 112 according to the fourth preferred embodiment of the present invention also includes the plurality of annual mounting tabs 42 linked together by the plurality of linking members 44 forming multiple internal peripheries or voids 78. The multi-configurable plate 112 can be used to form multiple conventional preconfigured plates such as T-shaped plates, L-shaped plates, Z-shaped plates, straight plates, and square-shaped plates, as well as multiple non-conventional shapes.

Figure 11:
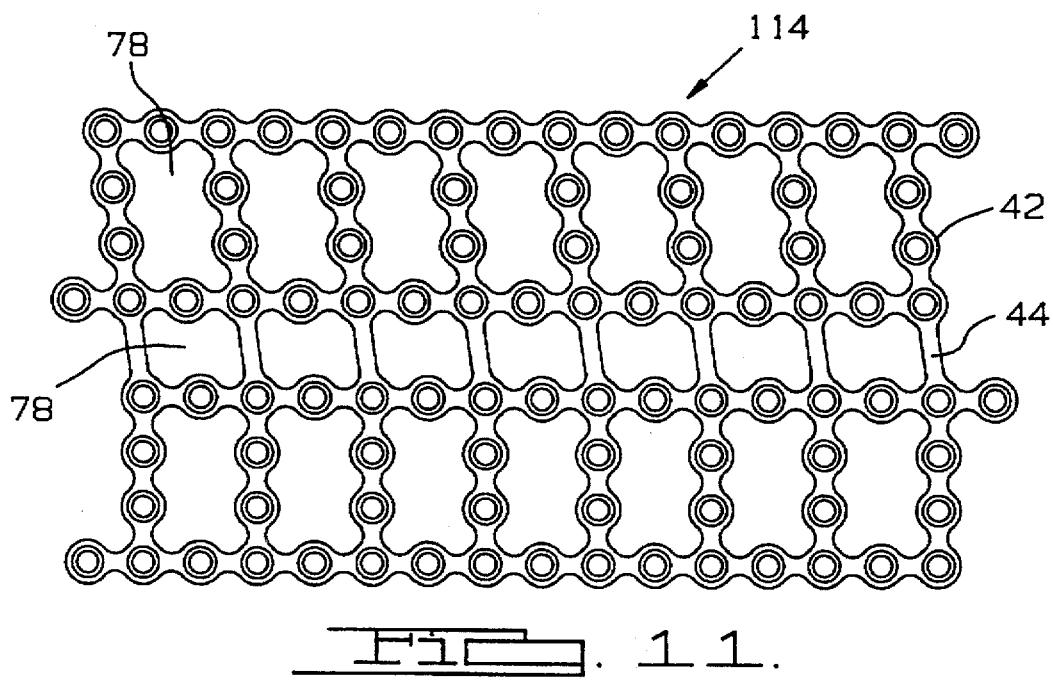
FIG. 11 is a top planar view of a multi-configurable plate according to the teachings of a fifth preferred embodiment of the present invention.

A fifth preferred embodiment of the present invention will now be described with reference to FIG. 11. A multi-configurable plate 114 according to the fifth preferred embodiment of the present invention also includes the plurality of annual mounting tabs 42 linked together by the plurality of linking members 44 forming multiple internal peripheries or voids 78. The multi-configurable plate 114 can be used to form several angled T-shaped plates, L-shaped plates, square plates and Z-shaped plates, non-angled T-shaped plates, square plates and L-shaped plates, as well as many other shaped plates.

Figure 12:
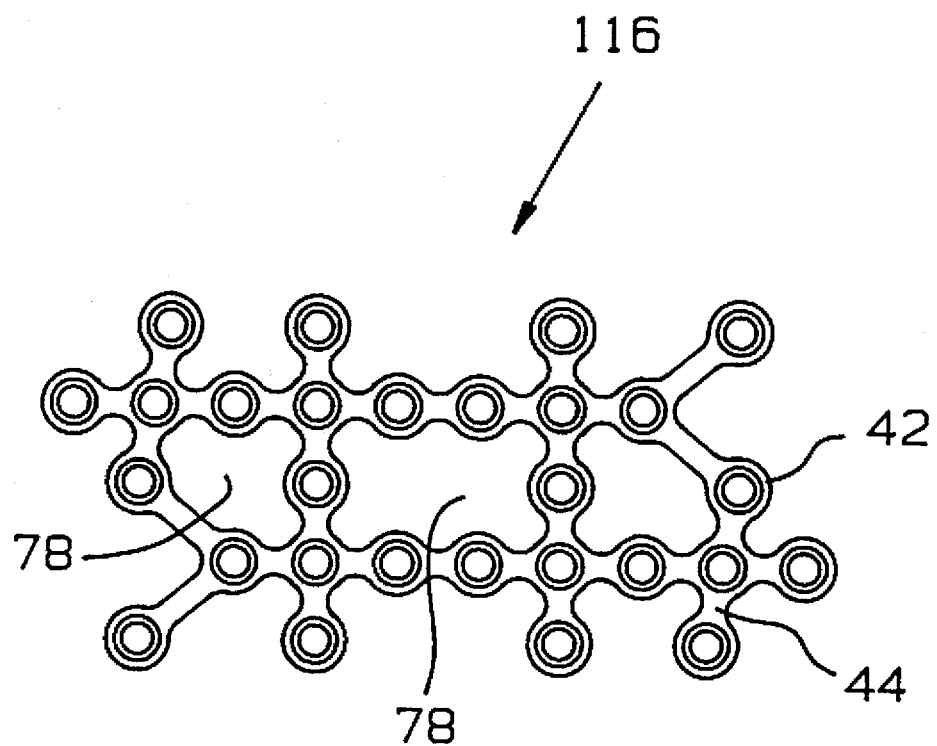
FIG. 12 is a top planar view of a multi-configurable plate according to the teachings of a sixth preferred embodiment of the present invention.

A sixth preferred embodiment of the present invention will now be described with reference to FIG. 12. A multi-configurable plate 116 according to the sixth preferred embodiment of the present invention also includes the plurality of annular mounting tabs 42 connected together by the plurality of linking members 44 to form multiple internal peripheries or voids 78. Here again, the multi-configurable plate 116 can be configured to create several conventional preconfigured shaped plates by merely cutting along the appropriate linking members 44. For example, it can be readily observed that the multi-configurable plate 116 can be used to form Y-shaped plates, T-shaped plates, X-shaped plates and numerous other conventional and non-conventional shaped plates.

Figure 13:
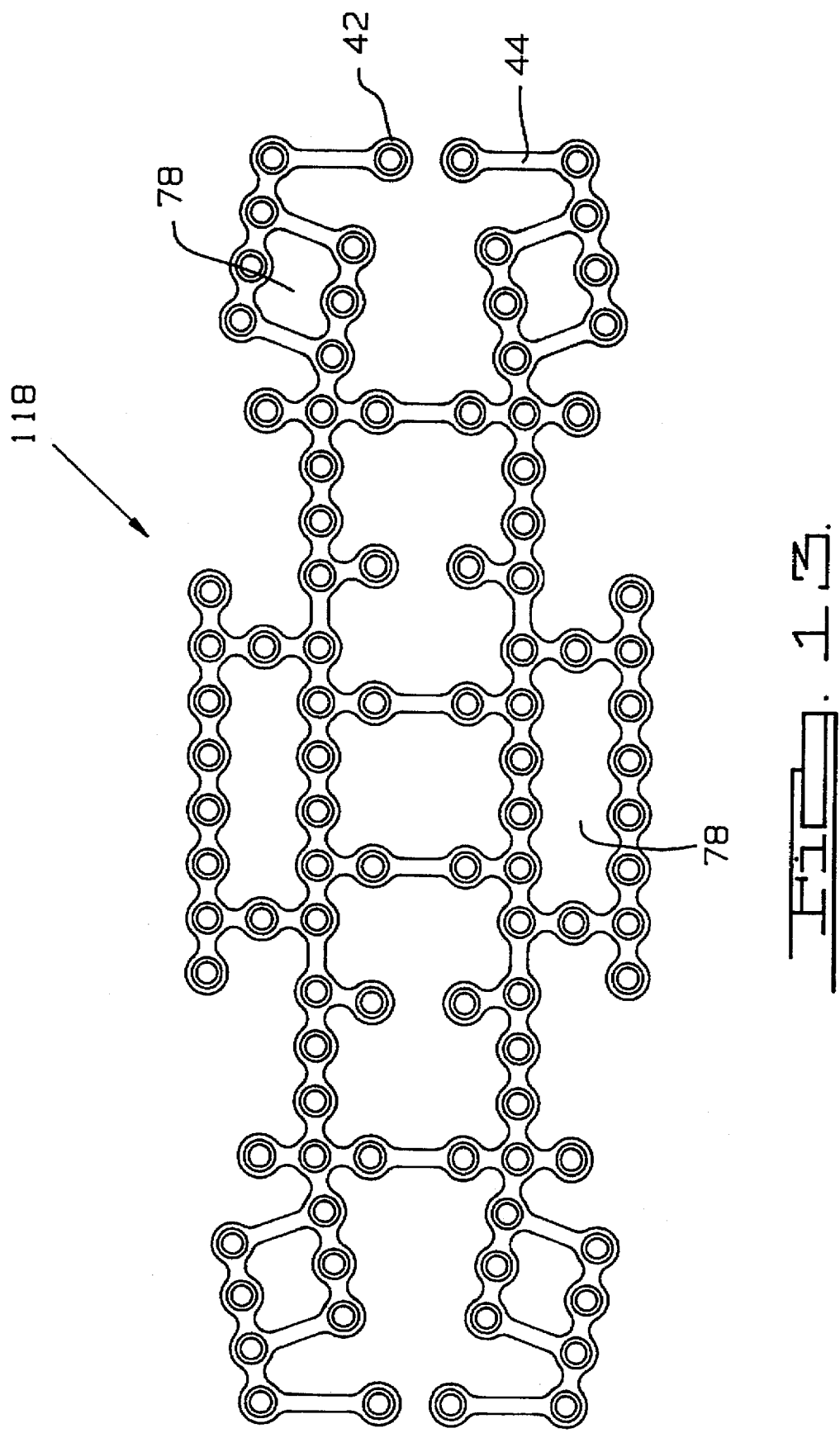
FIG. 13 is a top planar view of a multi-configurable plate according to the teachings of a seventh preferred embodiment of the present invention.

A seventh preferred embodiment of the present will now be described with reference to FIG. 13. The multi-configurable plate 118 according to the seventh preferred embodiment of the present invention is again formed by the plurality of annular mounting tabs 42 linked together with the plurality of linking members 44 forming multiple internal peripheries or voids 78. The multi-configurable plate 118 is a larger plate that is capable of forming almost all of the conventional preconfigured shapes, as well as numerous non-conventional shapes. Specifically, the multi-configurable plate 122 can form between approximately 40 to 50 conventional preconfigured shapes, including arcuate-shaped plates, T-shaped plates, L-shaped plates and straight plates.

The method of using the multi-configurable plating system will now be described as used in osteosynthesis surgical procedures. It is to be understood, however, that the multi-configurable plating system may be used with other surgical procedures as well. In addition, while the following procedure will be described in detail with regard to the first preferred embodiment of the multi-configurable plating system, those skilled in the art will recognize that the similar procedure would be applied to the other preferred embodiments as well.

Figure 1A:
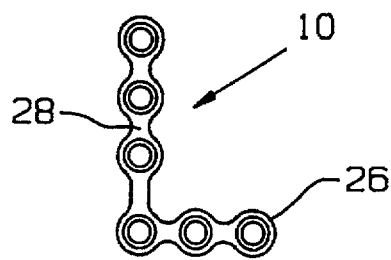
FIG. 1A is top planar view of a prior art preconfigured L-shaped plate.
Figure 1B:
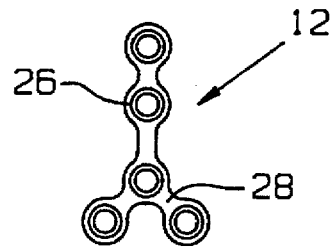
FIG. 1B is top planar view of a prior art preconfigured Y-shaped plate.
Figure 1C:
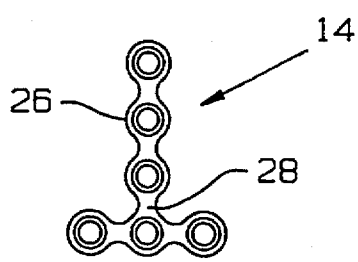
FIG. 1C is top planar view of a prior art preconfigured T-shaped plate.
Figure 1D:
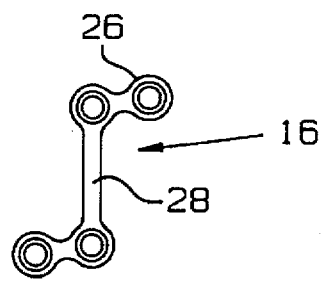
FIG. 1D is top planar view of a prior art preconfigured Z-shaped plate.
Figure 1E:
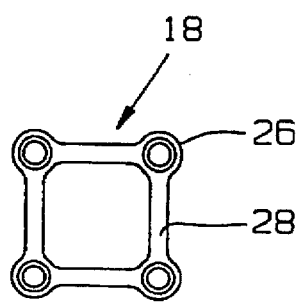
FIG. 1E is top planar view of a prior art preconfigured square-shaped plate.
Figure 1F:
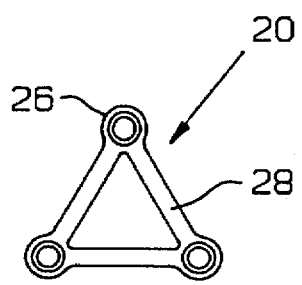
FIG. 1F is top planar view of a prior art preconfigured triangular-shaped plate.
Figure 1G:
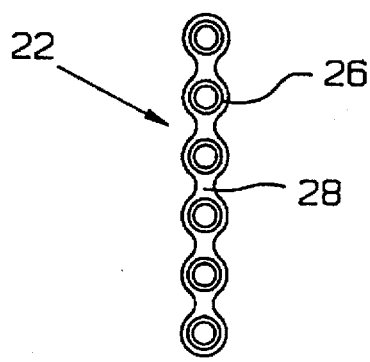
FIG. 1G is a top planar view of a prior art preconfigured straight plate.
Figure 1H:
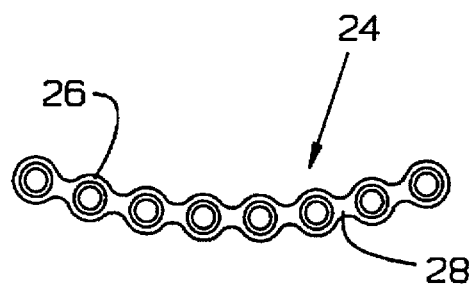
FIG. 1H is a top planar view of a prior art preconfigured arcuate-shaped plate.
Figure 2:
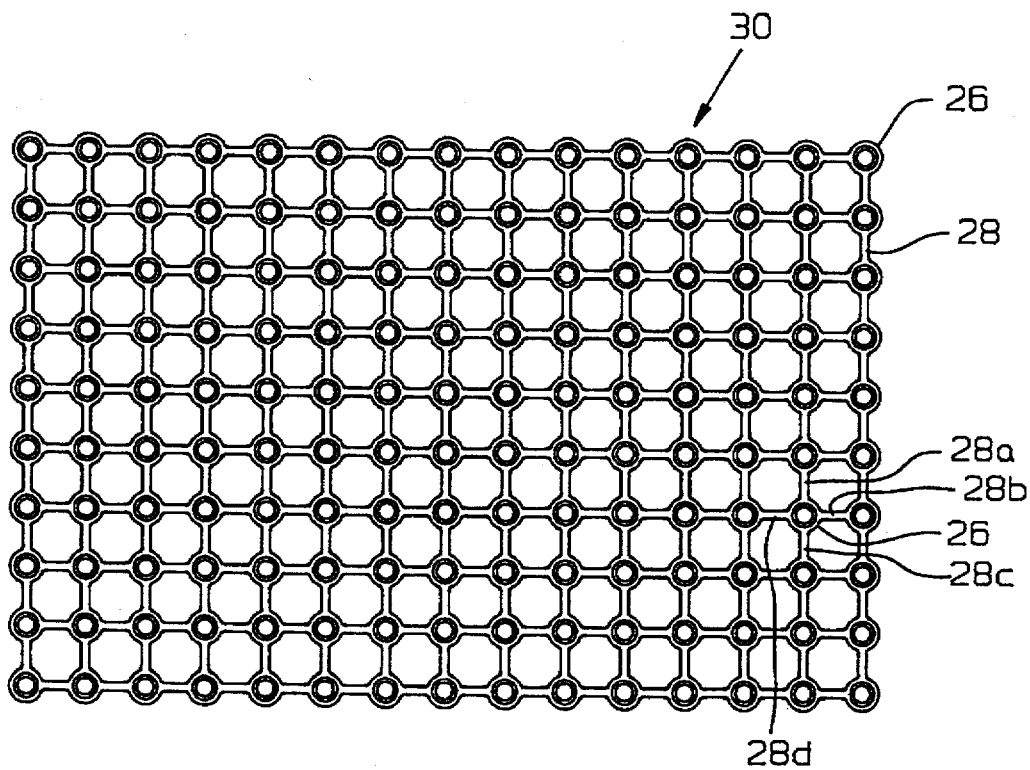
FIG. 2 is a top planar view of a prior art uniform grid panel.
Figure 3:
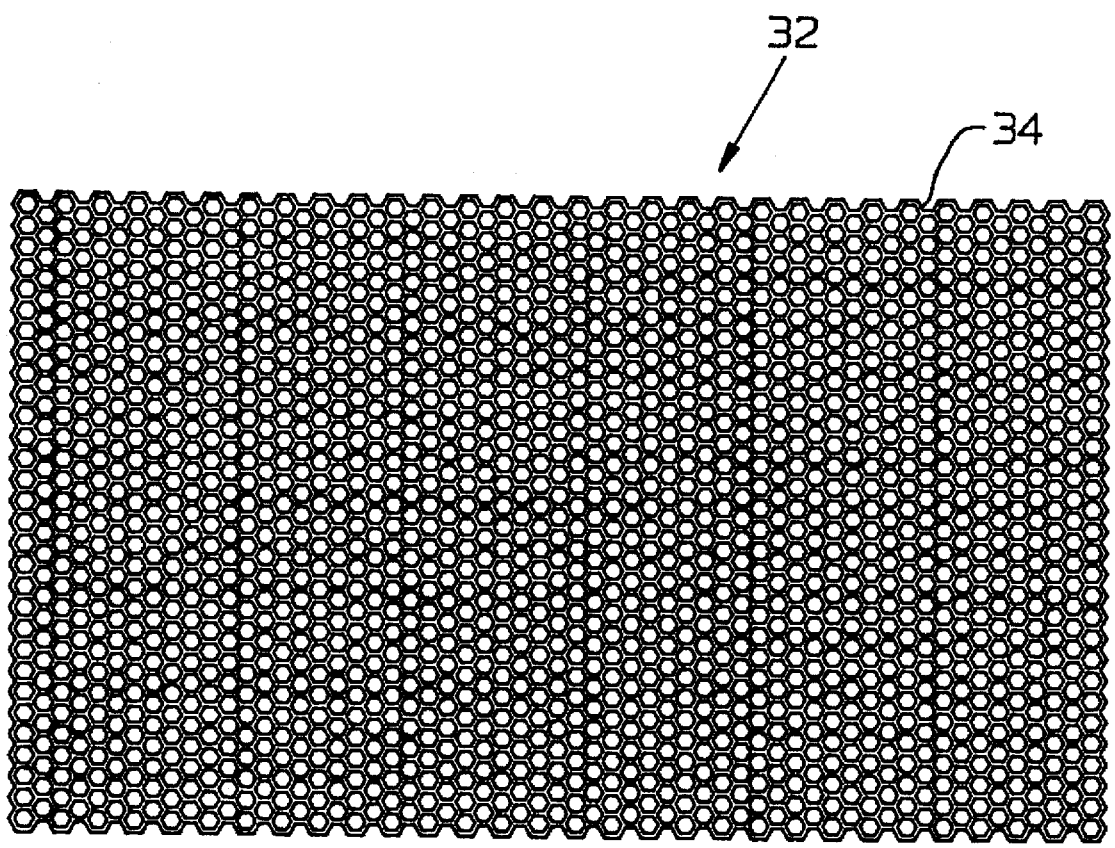
FIG. 3 is a top planar view of a prior art flexible mesh.
Figure 4:
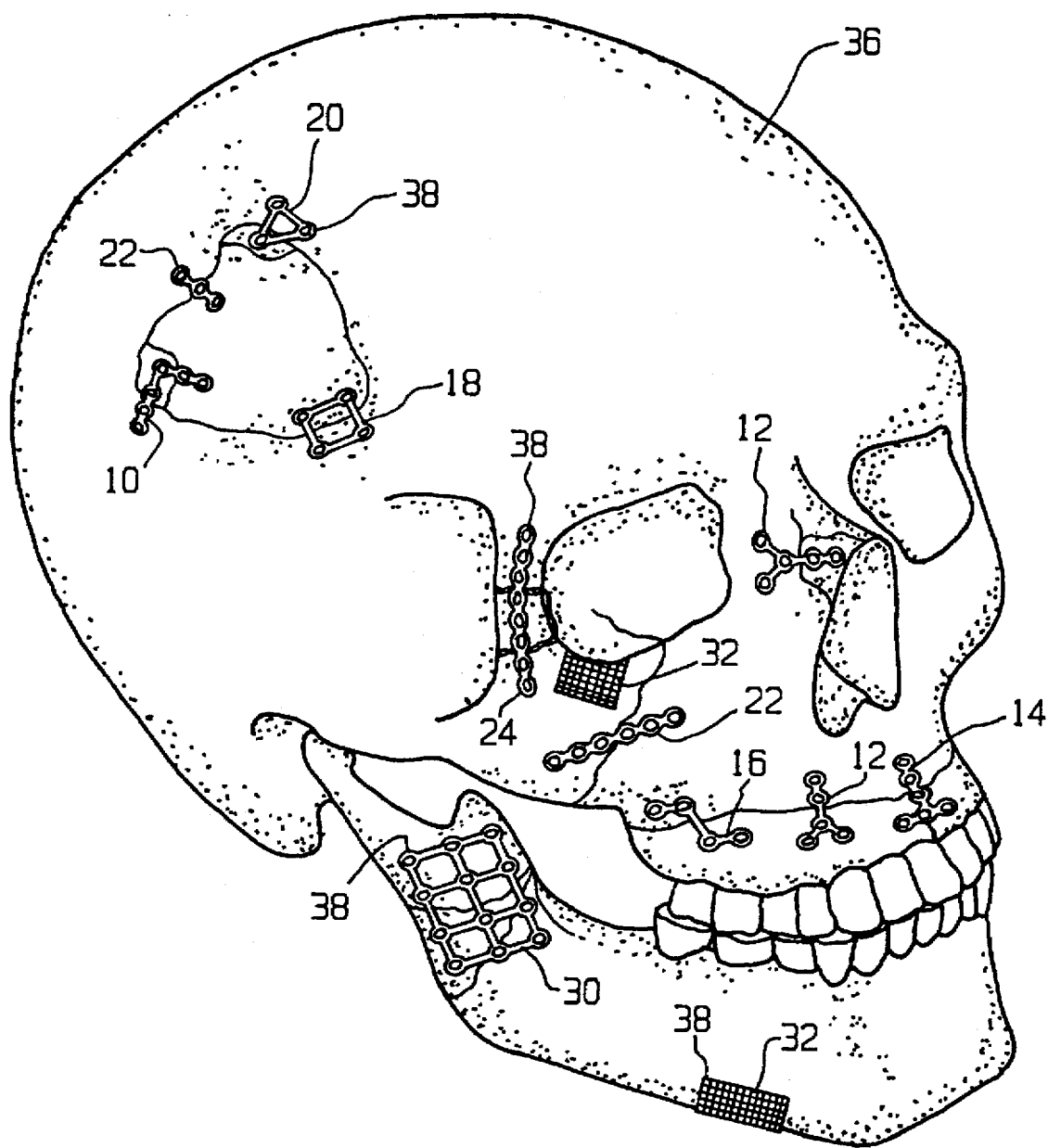
FIG. 4 is a perspective view of a skull which employs various mechanical devices.

Various multi-configurable plates 40 are first formed, having different thickness, as shown in FIG. 5. The surgeon then determines to what extent the plate will bear loads and can choose an appropriate thickness such as 0.6 mm or 1.0 mm. Once this is determined, the surgeon then determines which shapes will be required to surgically align, stabilize fixedly secure or retain two portions of the bone (see FIG. 4). This enables a surgeon to go into surgery with only one multi-configurable plate 40 capable of covering many procedures.

For example, should the surgeon determine that a straight plate, an L-shaped plate, and a T-shaped plate be required, the surgeon will cut along the appropriate linking members 44 to generate these desired shapes. Specifically, to form a straight plate 70, the surgeon will only be required to cut along generally two linking members, to form an L-shaped plate 72, the surgeon will also be required to only cut along generally two linking members, while to form a T-shaped plate 74, the surgeon will generally only be required to cut along three linking members. Upon cutting along these appropriate linking members, the surgeon may easily separate the separable straight plate 70, the separable L-shaped plate 72 and the separable T-shaped plate 74 from the multi-configurable plate 40. Once separated, each plate is appropriately secured to the skull 36 by bone screws 50 thereby holding one portion of the bone in a fixed relationship with respect to another portion of the bone.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A single multi-configurable plate for use in osteosynthesis, said single multi-configurable plate comprising:

a plurality of tabs connected together by a plurality of linking members;

an integral straight plate defined by at least three of said tabs and at least two of said linking members, said integral straight plate separable from said single multi-configurable plate by cutting along less than three of said linking members;

an integral L-shaped plate defined by at least three of said tabs and at least two of said linking members, said integral L-shaped plate separable from said single multi-configurable plate by cutting along less than three of said linking members; and an integral T-shaped plate defined by at least four of said tabs and at least three of said linking members, said Integral T-shaped plate separable from said single multi-configurable plate by cutting along less than four of said linking members, wherein a user may easily separate each of said integral straight plate, said integral L-shaped plate, and said integral T-shaped plate from said single multi-configurable plate by cutting along appropriate linking members.

2. The single multi-configurable plate as defined in claim 1 wherein said single multi-configurable plate is operable to define up to about 50 different integral plates having different shapes and separable from said single multi-configurable plate.

3. The single multi-configurable plate as defined in claim 1 further comprising an integral Z-shaped plate separable from said single multi-configurable plate by cutting along less than five of said linking members, wherein the user may further easily separate said integral z-shaped plate from said single multi-configurable plate by cutting along appropriate linking members.

4. The single multi-configurable plate as defined in claim 1 wherein said single multi-configurable plate is formed from a material selected from the group consisting of titanium, titanium alloy, cobalt chrome, resorbable polymer and stainless steel.

5. The single multi-configurable plate as defined in claim 1 wherein each tab includes a counterbore operable to receive a head of a screw.

6. The single multi-configurable plate as defined in claim 1 includes a first integral straight plate defined by a first plurality of said tabs and a first plurality of said linking members, a second integral straight plate defined by a second plurality of said tabs and a second plurality of said linking members, and a third integral straight plate defined by a third plurality of said tabs and a third plurality of said linking members, said second integral straight plate being substantially perpendicular to said first integral straight plate and said third integral straight plate being substantially oblique to said first integral straight plate.

7. A single multi-configurable plate for use in osteosynthesis, said single multi-configurable plate comprising:

a plurality of mounting tabs connected together by a plurality of linking members;

a first plurality of said mounting tabs and a first plurality of said linking members defining an integral straight plate separable from said single multi-configurable plate by cutting along less than three of said linking members;

a second plurality of said mounting tabs and a second plurality of said linking members defining an integral T-shaped plate separable from said single multi-configurable plate by cutting along less than four of said linking members; and a third plurality of said mounting tabs and a third plurality of said linking members defining an integral Z-shaped plate separable from said single multi- configurable plate by cutting along less than five of said linking members, wherein a user may easily separate each of said integral straight plate, said integral T-shaped plate, and said integral Z-shaped plate from said single multi-configurable plate by cutting along appropriate linking members.

8. The single multi-configurable plate as defined in claim 7 wherein a fourth plurality of said mounting tabs and a fourth plurality of said linking members defines an integral L-shaped plate separable from said single multi-configurable plate by cutting along less than three of said linking members, wherein the user may further easily separate said integral L-shaped plate from said single multi-configurable plate by cutting along appropriate linking members.

9. The single multi-configurable plate as defined in claim 7 wherein a fourth plurality of said mounting tabs and a fourth plurality of said linking members defines an integral arcuate-shaped plate separable from said single multi-configurable plate, wherein the user may further easily separate said integral arcuate-shaped plate from said single multi-configurable plate by cutting along appropriate linking members.

10. The single multi-configurable plate as defined in claim 7 includes a first integral straight plate defined by a fourth plurality of said mounting tabs and a fourth plurality of said linking members, a second integral straight plate defined by a fifth plurality of said mounting tabs and a fifth plurality of said linking members, and a third integral straight plate defined by a sixth plurality of said mounting tabs and a sixth plurality of said linking members, said second integral straight plate being substantially perpendicular to said first integral straight plate and said third integral straight plate being substantially oblique to said first integral straight plate.

11. A single multi-configurable plate for use in osteosynthesis, said single multi-configurable plate comprising:

a plurality of mounting tabs connected together by a plurality of linking members;

a first plurality of said mounting tabs and a first plurality of said linking members defining an integral straight plate separable from said single multi-configurable plate by cutting along less than three of said linking members;

a second plurality of said mounting tabs and a second plurality of said linking members defining an integral L-shaped plate separable from said single multi-configurable plate by cutting along less than three of said linking members; and a third plurality of said mounting tabs and a third plurality of said linking members defining an integral Z-shaped plate separable from said single multi-configurable plate by cutting along less than five of said linking members, wherein a user may easily separate each of said integral straight plate, said integral L-shaped plate, and said integral Z-shaped plate from said single multi-configurable plate by cutting along appropriate linking members.

12. The single multi-configurable plate as defined in claim 11 wherein a fourth plurality of said mounting tabs and a fourth plurality of said linking members defines an integral T-shaped plate separable from said single multi-configurable plate by cutting along less than four of said linking members, wherein the user may further easily separate said integral T-shaped plate from said single multi-configurable plate by cutting along appropriate linking members.

13. The single multi-configurable plate as defined in claim 11 wherein a fourth plurality of said mounting tabs and a fourth plurality of said lining members defines an integral arcuate-shaped plate separable from said single multi-configurable plate, wherein the user may further easily separate said integral arcuate-shaped plate from said single multi-configurable plate by cutting along appropriate linking members.

14. The single multi-configurable plate as defined in claim 11 includes a first integral straight plate defined by a fourth plurality of said mounting tabs and a fourth plurality of said linking members, a second integral straight plate defined by a fifth plurality of said mounting tabs and a fifth plurality of said linking members, and a third integral straight plate defined by a sixth plurality of said mounting tabs and a sixth plurality of said linking members, said second integral straight plate being substantially perpendicular to said first integral straight plate and said third integral straight plate being substantially oblique to said first integral straight plate.

15. A single multi-configurable plate for use in osteosynthesis having a plurality of mounting tabs and a plurality of linking members, said single multi-configurable plate comprising:

a first integral straight plate defined by a first plurality of said mounting tabs and a first plurality of said linking members;

a second integral straight plate defined by a second plurality of said mounting tabs and a second plurality of said linking members, said second integral straight plate being substantially parallel with said first integral straight plate;

a third integral straight plate defined by a third plurality of said mounting tabs and at least one of said linking members, said third integral straight plate being substantially perpendicular to said first and second integral straight plates and connected to said first and second integral straight plates by less than three linking members; and a fourth integral straight plate defined by a fourth plurality of said mounting tabs and at least one of said linking members, said fourth integral straight plate being oblique to said first and second integral straight plates and connected to said first and second integral straight plates by less than three linking members, wherein a plurality of integral plates may be separated from said single multi-configurable plate by cutting along appropriate linking members.

16. The single multi-configurable plate as defined in claim 15 wherein a fifth plurality of said mounting tabs and a fifth plurality of said linking members defines an integral L-shaded plate which is separable from said single multi-configurable plate by cutting along less than three of said linking members.

17. The single multi-configurable plate as defined in claim 15 wherein a fifth plurality of said mounting tabs and a fifth plurality of said linking members defines an integral T-shaped plate which is separable from said single multi-configurable plate by cutting along less than four of said linking members.

18. The single multi-configurable plate as defined in claim 15 wherein a fifth plurality of said mounting tabs and a fifth plurality of said linking members defines a Z-shaped plate which is separable from said single multi-configurable plate by cutting along less than five of said linking members.

19. A single multi-configurable plate for use in osteosynthesis, said single multi-configurable plate comprising:

a plurality of mounting tabs;

a plurality of linking members coupled to said plurality of mounting tabs; and said plurality of mounting tabs and said plurality of linking members defining a plurality of separate internal peripheries, each of said separate internal peripheries substantially devoid of said linking members and of said mounting tabs and bounded by at least three sides, at least one of said three sides of at least one of said separate internal peripheries each defined by at least four mounting tabs, wherein a plurality of integral plates defined by said plurality of mounting tabs and said plurality of linking members may be separated from said single multi-configurable plate by cutting along appropriate linking members.

20. The single multi-configurable plate as defined in claim 19 wherein each of said at least three sides is substantially straight.

21. The single multi-configurable plate as defined in claim 19 wherein at least one of said three sides is formed with at least three mounting tabs.

22. A single multi-configurable plate for use in osteosynthesis, said single multi-configurable plate comprising:

a plurality of mounting tabs;

a plurality of linking members coupled to said plurality of mounting tabs; and said plurality of mounting tabs and said plurality of linking members defining a plurality of separate internal peripheries, each of said separate internal peripheries substantially devoid of said linking members and of said mounting tabs and bounded by at least three sides, at least two of said three sides of at least one of said separate internal peripheries each defined by at least three mounting tabs, wherein a plurality of integral plates defined by said plurality of mounting tabs and said plurality of linking members may be separated from said single multi-configurable plate by cutting along appropriate linking members.

23. The single multi-configurable plate as defined in claim 22 wherein each of said at least three sides is substantially straight.

24. The single multi-configurable plate as defined in claim 22 wherein each of said at least three sides is formed from said plurality of mounting and said plurality of linking members.

25. A method for aligning and stabilizing a first portion of a bone relative to a second portion of the bone, said method comprising the steps of:

forming a single multi-configurable plate having a plurality of mounting tabs which are linked together by a plurality of linking members;

separating an integral straight plate defined by at least three of said mounting tabs and at least two of said linking members from said single multi-configurable plate by cutting along less than three of said linking members;

separating an integral L-shaped plate defined by at least three of said mounting tabs and at least two of said linking members from said single multi-configurable plate by cutting along less than three of said linking members; and separating an integral T-shaped plate defined by at least four of said mounting tabs and at least three of said linking members from said single multi-configurable plate by cutting along less than four of said linking members.

26. The method as defined in claim 25 further comprising the steps of separating an integral Z-shaped plate defined by a first plurality of said mounting tabs and a first plurality of said linking members from said single multi-configurable plate by cutting along less than five of said linking members.

27. The method as defined in claim 25 further comprising the steps of affixing said straight plate, said L-shaped plate and said T-shape plate to the bone by passing mounting screws through said mounting tabs.

* * * * *

UNITED STATES PATENT AND TRADEMARK OFFICE
CERTIFICATE OF CORRECTION

PATENT NO. : 5,690,631
DATED : November 25, 1997
INVENTOR(S) : Jeffrey Duncan; Kevin Stone It is certified that error appears in the above-identified patent and that said Letters Patent is hereby corrected as shown below:

Col. 6, line 3, "form" should be --four--.

Col. 7, line 23, insert "invention" after "present".

Col. 10, line 25, "lining" should be --linking--.

Col. 11, line 8, "shaded" should be "shaped".

Signed and Sealed this

Fourth Day of May, 1999

Q. TODD DICKINSON

Attest:

Attesting Officer

Acting Commissioner of Patents and Trademarks